United States Patent [19]

Evans et al.

[11] Patent Number: 4,991,128
[45] Date of Patent: Feb. 5, 1991

[54] APPARATUS AND METHODS FOR SPECTRAL ANALYSIS OF ELECTRICAL MATERIALS, COMPONENTS AND DEVICES

[75] Inventors: William A. Evans, Swansea, Wales; Alan Popplestone, Bexhill-on-Sea, England

[73] Assignee: National Research Development Corporation, London, England

[21] Appl. No.: 228,279

[22] Filed: Aug. 4, 1988

[30] Foreign Application Priority Data

Aug. 6, 1987 [GB] United Kingdom ............... 8718642

[51] Int. Cl.$^5$ .................................................. G01R 29/00
[52] U.S. Cl. .................................... 364/576; 364/480; 364/481
[58] Field of Search ........................ 324/57 R, 77 B; 364/482, 576, 579, 480, 481

[56] References Cited

U.S. PATENT DOCUMENTS

| | | | |
|---|---|---|---|
| 4,067,060 | 1/1978 | Poussart et al. | 324/77 B X |
| 4,286,326 | 8/1981 | Houdard | 324/77 B X |
| 4,301,404 | 11/1981 | Ley | 324/77 B |
| 4,402,054 | 8/1983 | Osborne et al. | 364/554 |
| 4,607,216 | 8/1986 | Yamaguchi et al. | 364/77 B |

FOREIGN PATENT DOCUMENTS 770280 3/1957 United Kingdom .
1426604 3/1976 United Kingdom .

Primary Examiner—Parshotam S. Lall
Assistant Examiner—Edward R. Cosimano
Attorney, Agent, or Firm—Cushman, Darby & Cushman

[57] ABSTRACT

Measurements of complex permittivity using transient techniques and Fourier transforms require computation which can be lengthy. In the invention, a synthesizer generates a succession of waveforms each containing a small number of harmonically related frequency components. These waveforms are applied to a capacitive potentiometer formed by a reference capacitor and a sample head. The voltages across the potentiometer and the sample head are passed by way of an analog-to-digital converter to a microprocessor which calculates Fourier transforms and indicates permittivity versus frequency. By limiting the frequency components, the computation time is reduced and a quick scan to find spectral regions of interest is possible. These regions can then be examined at higher resolution by changing a clock frequency which determines the generation of the frequency components.

10 Claims, 4 Drawing Sheets

APPARATUS AND METHODS FOR SPECTRAL ANALYSIS OF ELECTRICAL MATERIALS, COMPONENTS AND DEVICES

BACKGROUND OF THE INVENTION

The present invention relates to a spectrometer and spectral method for use with a test circuit containing a component or device whose properties are to be measured over a frequency range. The component may hold a sample of material whose electrical properties are to be determined over the frequency range.

The invention is particularly but not exclusively concerned with the measurement of complex permittivity. Known techniques of permittivity measurement divide into single-frequency (Q-meter, bridge, phase-sensitive-detector) and multi-frequency (transient-step response and pseudo-random-noise) techniques. Laboratory apparatus employed for the more exacting measurements appears to call for particular skills on the part of the user. Transient techniques have been of particular interest in recent years and heralded major advances in speed of measurements at low frequencies at an accuracy sufficient to satisfy many investigations.

SUMMARY OF THE INVENTION

According to a first aspect of the present invention there is provided apparatus for analysing the response of a circuit to signals of different frequencies, comprising synthesis means for generating a series of waveforms in which each waveform has a plurality of frequency components with frequencies in a geometric progression but no other significant frequency components, and the waveforms together having frequency components evenly spaced over a logarithmic spectrum, a test circuit coupled to receive the output of the synthesis means, and analysis means coupled to receive the output of the test circuit for repeatedly carrying out a respective Fourier analysis on signals received from the test circuit resulting from the application thereto of each of different groups of the said waveforms.

Usually the frequency components of each waveform are separated from one another by an octave, and each said group contains one waveform only (thus the number of groups equals the number of waveforms).

Advantages of a logarithmic spectrum composed of small sized fast Fourier transforms include inherently fast computation, the possibility of a "quick look" scan to find spectral regions of interest, and spectral information at intervals which are well suited to measurements of polymers exhibiting single-relaxation phenomena.

The synthesis means may comprise means for providing a clock signal, a store which stores samples of a single period of one of the waveforms and sample-reading means for repeatedly reading out the stored samples at rates related to the frequency of the clock signal in generating the series of waveforms. The synthesis means may then include means for varying the frequency of the clock signal from time to time by substituting a new clock signal having a frequency which is an integral multiple or submultiple of a previous clock-signal frequency, such that the frequency components of the waveforms are evenly spaced over the logarithmic spectrum.

In order to allow the spectrum to be examined at higher frequency resolution the synthesis means may include means for changing the clock signal frequency by an increment such that resulting waveforms generated by the synthesis means over at least part of the said spectrum have frequency components which are evenly spaced on a logarithmic basis from the components of waveforms generated before the increment was applied.

The test circuit may comprise a two capacitor potentiometer if permittivity is to be measured; one capacitor being an adjustable reference capacitor and the other capacitor forming a holder for a sample of the dielectric whose permittivity is to be measured. The analysis means may then comprise an analogue-to-digital (ADC) converter, two-state switch means for connecting the input of the ADC to one end of the potentiometer in one state and, by way of an amplifier of fixed gain, to the connection between the capacitors in the other state. If the reference capacitor is adjusted to give a capacitance ratio between its capacitance and that of the sample holder when containing the sample, the amplifier can provide a signal output which ensures that the ADC receives signals covering substantially its entire input voltage range in both switch states. For other types of measurement other types of impedance may be used to form the potentiometer.

According to a second aspect of the invention there is provided a method of analysing the response of a circuit to signals of different frequencies, comprising the steps of generating a series of waveforms in which each waveform has a plurality of frequency components with frequencies in a geometric progression but no other significant frequency components, and the waveforms together having frequency components evenly spaced over a logarithmic spectrum, applying the series of waveforms to a test circuit and repeatedly carrying out a respective Fourier analysis on signals received from the test circuit which result from the application of each of the said waveforms thereto.

According to a third aspect of the invention there is provided apparatus for determining the frequency response of a circuit, comprising means for applying a series of waveforms each containing a plurality of frequency components to a sample material or device, and analysis means for receiving signals from the material or device and analysing the received signals in the frequency domain.

The invention also includes a method corresponding to the third aspect of the invention.

BRIEF DESCRIPTION OF THE DRAWINGS

Certain embodiments of the invention will now be described with reference to the accompanying drawings, in which.

DESCRIPTION OF THE PREFERRED EMBODIMENTS

Figure 1:
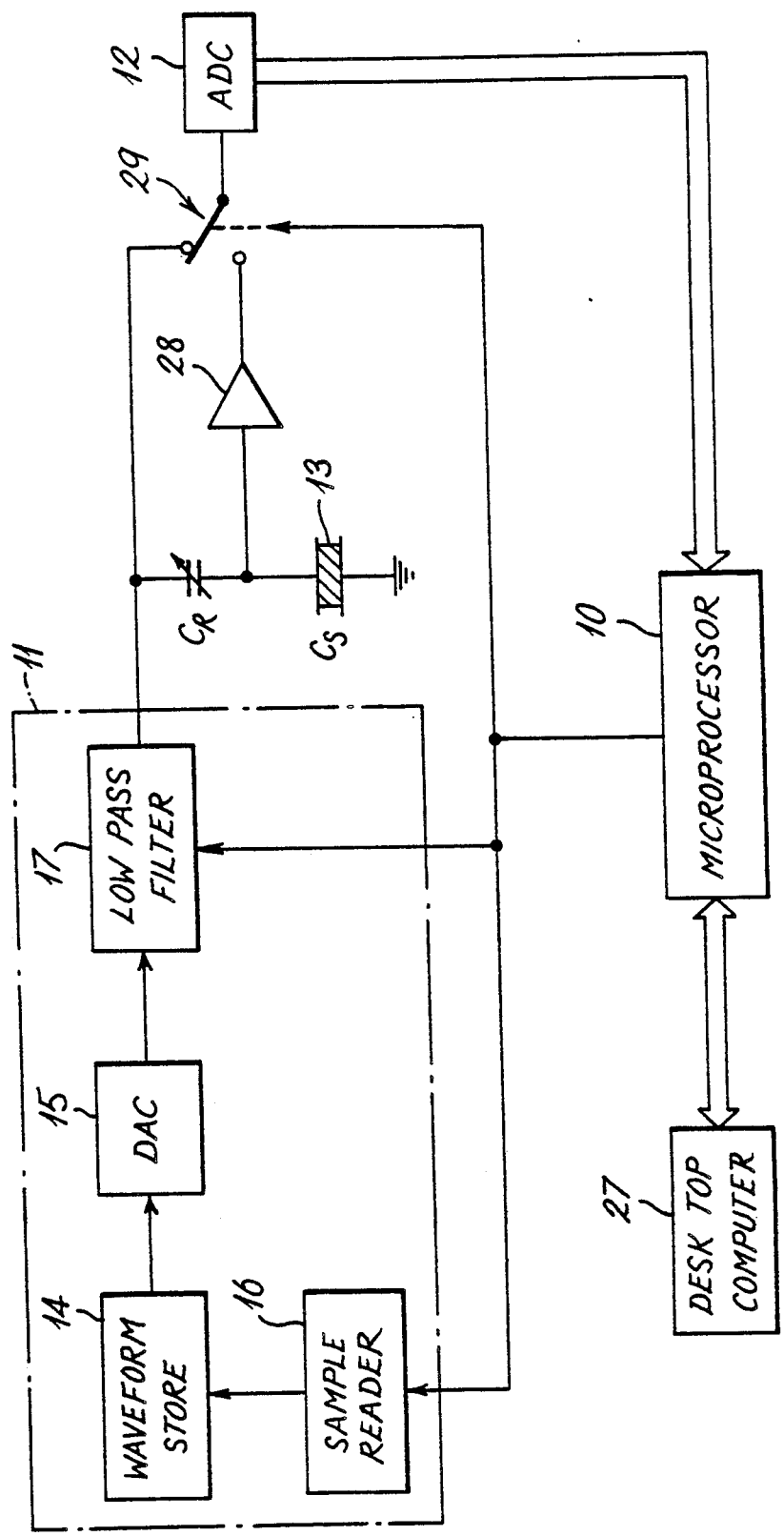
FIG. 1 is a block diagram of an embodiment of the invention for permittivity measurement.

The apparatus of FIG. 1 is used to carry out a ratiometric measurement which allows the relative permittivity of a sample to be calculated by a microprocessor 10. A succession of voltage waveforms each containing three frequency components is generated by a synthesiser 11 and passed to a capacitive potentiometer formed by a reference capacitor $C_R$ and a sample head $C_S$. The resulting voltages across the potentiometer and across the sample head are sampled by an analogue to digital converter (ADC) 12 and passed to the microprocessor 10. The synthesiser 11 generates a succession of waveforms each with components in a respective frequency range so that the frequency components of all the waveforms are together spread evenly on a logarithmic scale across a bandwidth in which permittivity is to be measured. At least two sets of measurements at all frequencies concerned are required, one with the sample holder $C_S$ empty and one with the sampler holder containing a sample 13 of the material whose permittivity is to be measured. A desk top computer 27 coupled to the microprocessor 10 can be used to control the measurements made.

The voltage equation with the sample absent is given by $$\frac{V_{VO}^*}{V_{SO}^*} = 1 + \frac{C_R}{C_S}$$

where $V_{VO}^*$ represents the complex voltage across the series combination of capacitor $C_R$ and the sample holder $C_S$, $V_{SO}^*$ represents the complex voltage across the sample holder $C_S$ and the capacities of these components are represented by their designations $C_R$ and $C_S$.

When the sample is inserted in the holder $$\frac{V_{VI}^*}{V_{SI}^*} = 1 + \frac{C_R}{k^* C_S}$$

where $V_{VI}^*$ represents the complex voltage across the series combination of capacitor $C_R$ and the sample holder $C_S$, $V_{SI}$ represents the complex voltage across the sample holder $C_S$ and $k^*$ represents the complex relative permittivity of the sample material. From which $$k^* = \frac{\left(\frac{V_{VO}^*}{V_{SO}^*} - 1\right)}{\left(\frac{V_{VI}^*}{V_{SI}^*} - 1\right)} \quad \text{equation 1}$$

Expressing equation 1 in terms of frequency $$k^*(\omega) = \frac{|Y(\omega)| < \theta_1(\omega)}{|X(\omega)| < \theta_2(\omega)} = \frac{|Y(\omega)|}{|X(\omega)|} < \theta_1(\omega) - \theta_2(\omega) \quad \text{equation 2}$$

Equation 2 is obtained by taking the Fourier Transform of the respective voltages of equation 1. The quotient can be represented in polar form by using CORDIC arithmetic due to Volder (see "The CORDIC Trigonometric Computing Technique", I.R.E. Trans. on Electronic Computers, Sept. 1959, pp. 330–334.

The voltages in equation 1 are taken as samples by the ADC 12 and the permittivity is found for each component frequency of each waveform by using the microprocessor 10 to calculate the Fourier transform of the respective voltages of equation 1 and thence to calculate the relative permittivity $k^*$ ($\frac{y}{x}$) at each frequency.

The waveforms generated by the synthesiser 11 are based on four composite waveforms held as 16-bit samples in a read only memory (ROM) waveform store 14. The four waveforms have the following respective groups of component frequencies:

f
f 2f 4f
f 3f
f 3f 7f.

Figure 2A:
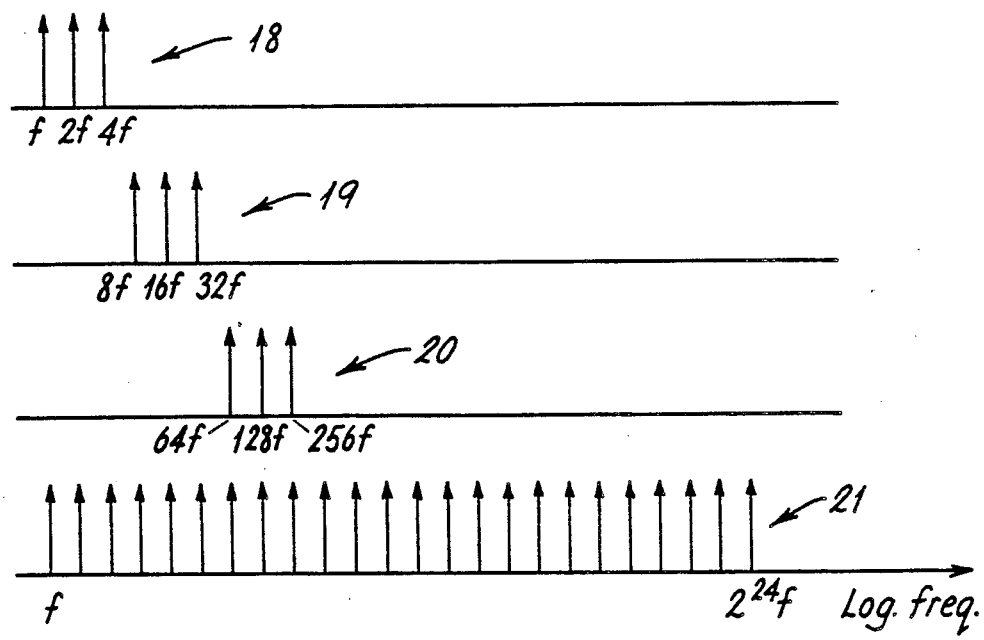
FIGS. 2a and 2b show spectra of waveforms generated by the synthesiser of FIG. 1.

Samples from the waveform store 14 are read out to a digital-to-analogue converter (DAC) 15 under the control of a sample reader 16 and the output of the DAC passes through a variable cut-off low pass filter 17 before being applied to the capacitive potentiometer. The spectra of three waveforms generated by the synthesiser 11 are shown at 18, 19 and 20 in FIG. 2a. Each waveform contains three frequency components and these components are arranged one octave apart, this spacing being maintained from one waveform to the next. The synthesiser 11 cycles through a group of waveforms to generate a complete spectrum 21 from a fundamental frequency f to a maximum frequency of $2^{24}f$, with the spectra produced being evenly spaced on a log-frequency basis.

Two methods are used to change the repetition frequency of output waveforms: the system clock frequency within the synthesiser 11 is varied as well as the number of output samples contained within one period. As shown in the accompanying Table, four changes of clock frequency are made in a complete cycle to form the spectrum 21 and with each of these clock frequencies the number of samples varies from 2,048 for the lowest frequency to 64 for the highest frequency.

TABLE

| | Clock Frequency | | | | | | | |
|---|---|---|---|---|---|---|---|---|
| | $f_c$ | $2f_c$ | $4f_c$ | $8f_c$ | $16f_c$ | $32f_c$ | | |
| | Number of Samples per Period | | | | | | Clock Frequency | |
| | 2048 | 1024 | 512 | 256 | 128 | 64 | (MHz) | Filter Span |
| Waveform Number Frequencies | | 6 | | | 7 | | | |
| | 488 Hz | 976 Hz | 1.95 kHz | 3.9 kHz | 7.8 kHz | 15.6 kHz | $2^0$ | 3 |
| | | 4 | | | 5 | | | |
| | 7.6 Hz | 15.3 Hz | 30.5 Hz | 61 Hz | 122 Hz | 244 Hz | $2^{-6}$ | 2 |
| | | 2 | | | 3 | | | |
| | 0.12 Hz | 0.24 Hz | 0.48 Hz | 0.95 Hz | 1.9 Hz | 3.8 Hz | $2^{-12}$ | 1 |
| | | 0 | | | 1 | | | |
| | 1.86 mHz | 3.73 mHz | 7.45 mHz | 15 mHz | 30 mHz | 60 mHz | $2^{-18}$ | 0 |

The low pass filter 17 has four spans as indicated in the last column of the Table and these spans are brought into operation as required by the microprocessor 10 as the synthesiser frequency output is varied. The lowest span has a pass band extending to 2 Hz and the highest span has a cut-off frequency of 20 kHz. For the frequencies given in the Table it has been found that the 60 dB attenuation given by the filter 17 together with the attenuation of harmonics given by the number of samples chosen per period ensure that any harmonics above 32 $f_c$ are below 91 dB.

As explained above one of the advantages of the system described is that a 16-point fast Fourier transform (FFT) is sufficient to separate out the response of the three frequency components of each waveform. The FFT only has to be carried out eight times in order to cover the whole frequency spectrum from 1.86 mHz to 15.6 kHz. Since the FFT technique and its implementation by a microprocessor is well known it will not be described in this specification.

The desk top computer 27 can be used to control the size of the spectrum spanned by the components of the waveforms from the synthesiser 11 (that is to control the number of waveforms synthesised). This allows advantage to be taken of the small sized FFTs in quickly investigating regions of the spectrum.

Figure 2B:
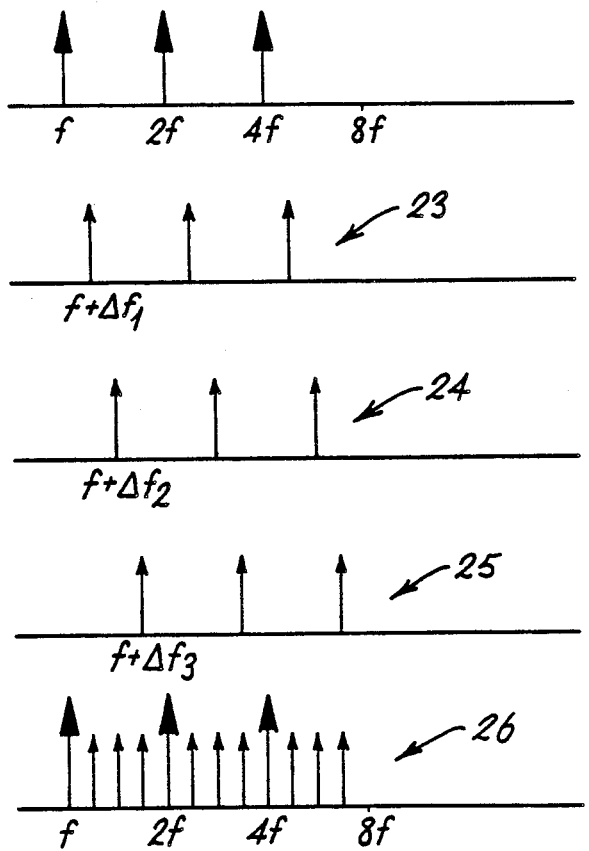

If a particular part of the frequency spectrum is revealed by frequency scanning as requiring more detailed examination then it is possible to zoom in on that part of the spectrum by offsetting the synthesiser clock for that part of the spectrum to $f + \Delta f$. The offset process can be repeated a number of times as shown in FIG. 2b at 23, 24 and 25 over an octave interval so that a relatively high resolution spectrum of input frequencies shown at 26 is obtained. Once again an FFT is carried out for each waveform (as represented for example by the components 23). Selection of clock frequency for the zoom technique can be controlled by the desk top computer 27.

In order to make full use of the dynamic range of the ADC 12 the centre point of the capacitive potentiometer is connected to an amplifier 28 having a gain of two. In operation the reference capacitor $C_R$ is adjusted so that it is approximately equal to the capacitance of the sample holder when the sample holder contains the sample 13. In this way the output of the amplifier 28 is approximately equal to the voltage at the upper end (as seen in FIG. 1) of the capacitive potentiometer. A multiplexer 29, represented as a switch, is used to allow samples of the voltages shown in equation 1 to be read by the ADC 12. As a result of the amplifier 28 the peak values of these voltages can be arranged to be always near the maximum allowed input voltage of the ADC 12.

A suitable ADC is likely to have a minimum conversion time which is much greater than sample intervals in the upper two frequency waveforms 6 and 7 (see Table). This problem can be overcome by an aliassing technique in which for these waveforms the first sample is taken, under the control of the microprocessor, by the ADC 12 at the start of the first cycle of the waveform concerned and then the next sample is taken after a complete cycle of the waveform plus one sample period, the procedure being carried out until all 16 samples required for the FFT have been taken.

Figure 3:
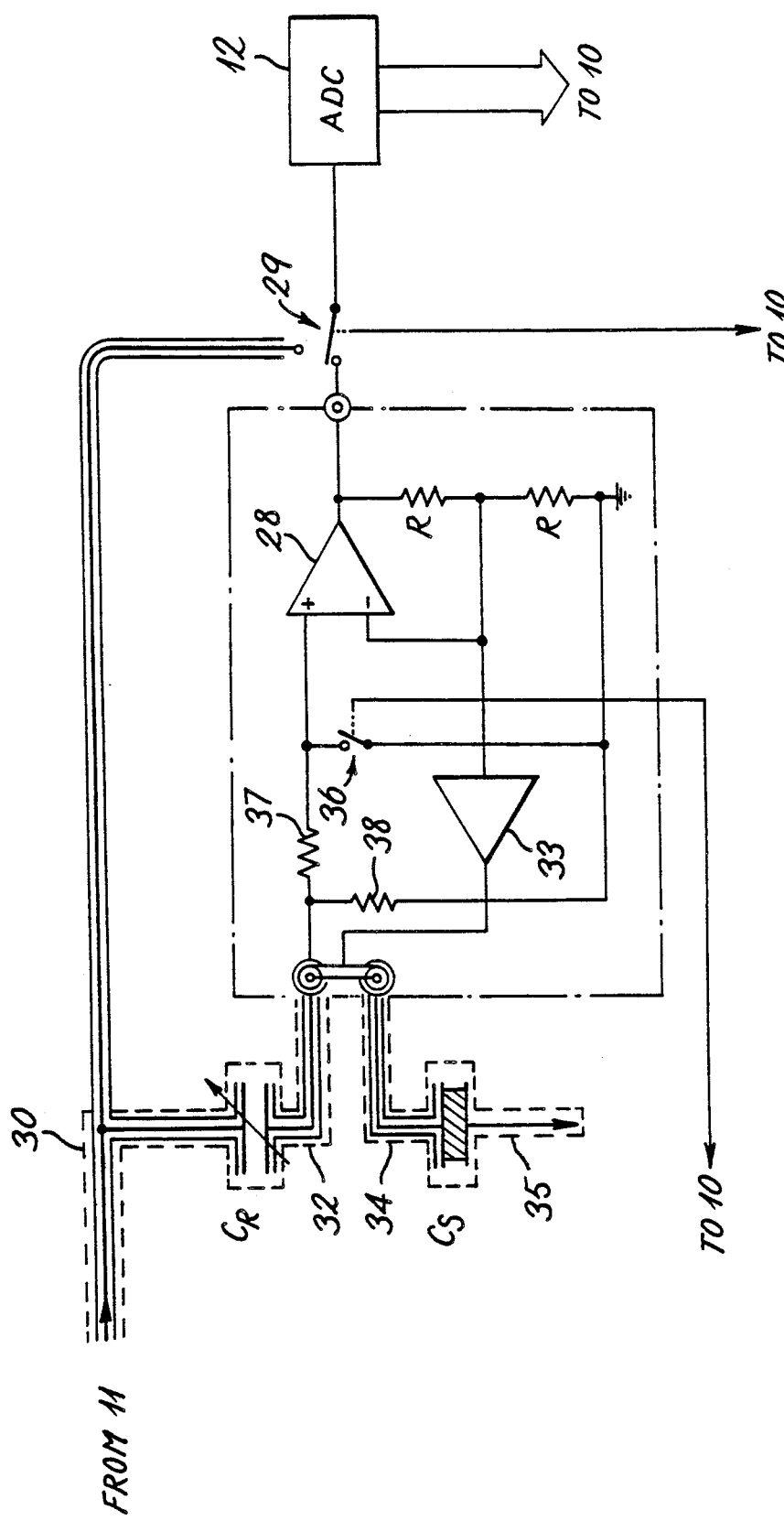
FIG. 3 shows part of the apparatus of FIG. 1 in more detail.

Special precautions have, of course, to be taken in order to provide shielding and to overcome the problems of unwanted capacities. The excitation signal is fed from the synthesiser 11 to the top plate of the variable reference capacitor $C_R$ through a 1 meter length of triaxial cable 30 (see FIG. 3). The lower plate of this capacitor is connected to the mid-point of the capacitive potentiometer by a 1 meter length of triaxial cable 32 which has its inner shield driven by an amplifier 33. The specimen holder $C_S$ is connected to the mid-point in a similar fashion by means of a 1 meter triaxial cable 34 and its other plate is returned to the signal ground by a coaxial cable 35. (No second screen is required because the inner conductor is at ground potential.) The operational amplifier 28 connected at the mid-point is an extremely low bias current type and therefore acts as an accurate buffer stage with a gain of 2. The operational amplifier is mounted by PTFE stand-offs to increase leakage impedance. Two equal resistors R provide an input for the amplifier 33 which has unity gain and therefore drives the inner shield of the triaxial cables 32 and 34 at the same voltage as the central conductor. The ratiometric measurement cancels out any phase or gain error that the two matched resistors R may introduce should they exhibit any reactive component.

A normally closed reed relay 36 together with a 47K Ohm resistor 37 and a $10^{10}$ Ohm resistor 38 provide protection for the low bias current amplifier 28. The reed relay 36 is opened just prior to a data acquisition period and is closed immediately afterwards. The moment of opening the reed relay 36 is very important for, once it opens, the operating circuitry has a very long time constant and requires a long period before settling down to a steady state around zero volts. The time constant is determined by the parallel combination of the reference capacitor and the sample capacitance with the resistor 38 giving a value of about 5 seconds for a specimen capacitance of 500 pF. For this reason a novel opening sequence is employed. At high frequencies the filter 17 is first shut down to its lowest cut off frequency (2 Hz) then after a delay to allow for settling the reed relay 36 is opened. After a second delay to allow for switch bounce the filter is returned to its original setting. At low frequencies, when the filter is already set to the lowest frequency range of 2 Hz, the zero crossing point of the signal is used to switch the relay.

Figure 4:
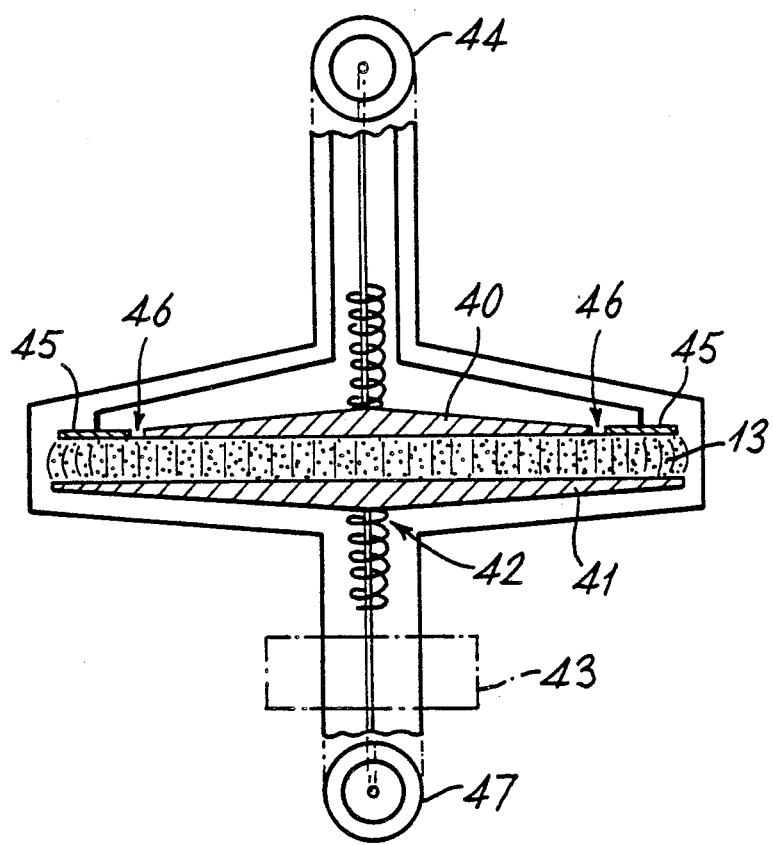
FIG. 4 shows a dielectric sample holder in the form of a capacitor for use in the apparatus of FIG. 1.

The specimen holder, made from gold plated brass, sandwiches the sample dielectric 13 between two flat circular electrodes 40 and 41 to form a parallel-plate capacitor as shown in FIG. 4. The lower plate, the larger of the two and supported by a ball joint at 42 to allow for non-parallel sides specimens, is spring loaded to ensure good electrical contact with the sample. In addition to this, electrodes are usually evaporated on to both sides of the sample specimen to improve electrical contact. A micrometer 43 provides a measure of the plate separation and is electrically insulated from the electrodes by PTFE washers. This lower plate is electrically connected to the signal ground.

The active area of the upper plate is driven by the central conductor of a triaxial socket 44. The inner screen of the socket drives the guard ring 45 which completely surrounds and is co-planar with this upper plate but electrically insulated from it by an air gap 46 of about 0.5 mm. The guard totally screens the upper plate from all other connections. Since the guard ring is driven by a signal of the same voltage and phase as the central plate, the only capacitance the central plate "sees" is that of the sample. This results in the flux lines permeating the specimen uniformly and perpendicularly across the whole active area since the fringing effects are transferred to the outer perimeter of the guard ring. All stray parasitic capacitances are driven by the guard voltage source and not the excitation source. A triaxial socket 47 is used to connect the lower plate but as mentioned above the connector 35 taken to this socket is coaxial. The triaxial socket 47 is used to allow $C_R$ and $C_S$ to be interchanged.

The voltage across and the current through a capacitor containing a dielectric may be measured and the permittivity of the dielectric calculated as an alternative method of determining permittivity. For this method the capacitive potentiometer is replaced by the sample holder (containing the sample) and a current measuring device is placed in series with the sample holder. Waveforms covering a desired frequency range are then applied to the sample holder and voltages and currents sampled by the ADC. Finally, FFTs are carried out for the voltages and currents and calculations of permittivity made by the microprocessor.

It will be realised that the dielectric spectrometer of the invention is a versatile instrument and is not limited to the measurement of dielectric parameters.

An application is an LCR multi-frequency component meter where the equivalent circuit (series or parallel) at each frequency may be computed.

The additional feature of harmonic evaluation by the discrete Fourier transform provided by the invention is useful when measuring non-linear components with single frequency excitation. An anti-aliassing filter is used to precede the track/hold input of the ADC 12 to prevent aliassing occurring. In addition it is useful to make the variable reference capacitor self-adjusting so that it equals the impedance of an unknown component. Two possible methods may be used: firstly by switching in fixed capacitors instead of a continuously variable capacitor and secondly by making use of a stepper motor to drive the shaft of a variable capacitor. A first ratiometric measurement is carried out with the unknown component in circuit instead of the sample holder $C_S$ and then a further reference capacitor is substituted for the unknown component to make the second ratiometric measurement. Selection of the stable binarily-related capacitors is required to cover the full range of possible unknown component capacities so that the mid-point voltage signal from the capacitive potentiometer is optimised for maximum accuracy.

Another application for the invention lies in the field of semiconductor devices. Evaluation of the "impurity profile" of PN-junctions and the free carrier density distributions, in addition to trap densities and their positions within the band-gap are vital pieces of information to the semiconductor physicists. Deep level (close to the middle of the band-gap) information relating to the generation and recombination of electron-hole pairs which contribute to the leakage current of PN-junctions is also important. These parameters are all functions of frequency, bias voltage and temperature, requiring a large amount of data to be collected. Automating this data collection brings considerable benefits since present point-by-point measurement methods are time-consuming. A few hardware modifications to the apparatus specifically described are necessary to adapt it for semiconductor measurements. The dynamic range of the excitation source of the instrument must be attenuated to about 10 mV peak. This is superimposed onto a DC bias voltage provided by an additional DAC connected to the current summing point of the output operational amplifier. The dynamic range of the bias voltage needs to cover the range of ±20 volts. A set of measurements, covering the whole frequency range of the instrument, is performed at each setting of bias voltage. As the bias voltage is stepped through the energy bandgap, any traps present at the particular potential couple in with the AC excitation signal, similar to dipole coupling in insulators, contributing to the loss factor of conductance in this case.

Measurements on metal-oxide-semiconductor (MOS) devices similarly provide information concerning the quality of the oxide and therefore about the resulting interface states. The presence of these interface states results in the increase in the threshold voltage of the MOS devices. Similar curves are obtained for the capacitance and conductance $(G/\omega)$ of the interface states versus log frequency as those obtained in dielectric measurements. The peak of conductance of the curve occurs at the trapping frequency. Its peak and width lead to the evaluation of the interface state density while the peak frequency is used to calculate the capture cross section for the majority carriers.

We claim:

1. Apparatus for analyzing the response of a circuit to signals of different frequencies, comprising
    synthesis means for generating a series of waveforms in which each waveform has a plurality of frequency components with frequencies in a geometric progression but no other significant frequency components, and the waveforms together having frequency components evenly spaced over a logarithmic spectrum,
    a test circuit coupled to receive the output of the synthesis means, and
    analysis means coupled to receive the output of the test circuit for repeatedly carrying out a respective Fourier analysis on signals received from the test circuit resulting from the application thereto of each of said waveforms to analyze a response thereof.

2. Apparatus according to claim 1 wherein the frequency components of each waveform are separated from one another by an octave.

3. An apparatus as in claim 1, wherein one of the impedances is constructed to hold a sample of non-conducting material whose permittivity is to be determined, and said analysis means further comprises means for determining a permittivity of said sample.

4. Apparatus according to claim 1 wherein the synthesis means comprises means for providing a clock signal, a store which stores samples of one of the waveforms, and sample-reading means for repeatedly reading out the stored samples at rates related to the frequency of the clock signal in generating the series of waveforms.

5. Apparatus according to claim 4 wherein the synthesis means includes means for varying, from time to time, the number of samples of the stored waveform which are read out in one period of the generated waveform.

6. Apparatus according to claim 4 wherein the synthesis means includes means for varying the frequency of the clock signal from time to time by substituting a new clock signal having a frequency which is an integral multiple or sub-multiple of a previous clock signal frequency, such that the frequency components of the waveforms are evenly spaced over the logarithmic spectrum.

7. Apparatus according to claim 6 including means for changing the clock signal frequency by an increment such that resulting waveforms generated by the synthesis means have frequency components which are evenly spaced on a logarithmic basis from the components of waveforms generated before the increment was applied.

8. Apparatus for analyzing the response of a circuit to signals of different frequencies, comprising
synthesis means for generating a series of waveforms in which each waveform has a plurality of frequency components with frequencies in a geometric progression but no other significant frequency components, and the waveforms together having frequency components evenly spaced over a logarithmic spectrum,
a test circuit coupled to receive the output of the synthesis means, wherein the test circuit comprises two impedances connected in series the test circuit being connected to receive the output of the synthesis means, and at least one of the impedances being adjustable to allow the impedances to have a predetermined impedance ratio,
analysis means coupled to receive the output of the test circuit for repeatedly carrying out a respective Fourier analysis on signals received from the test circuit resulting from the application thereto of each of the said waveforms, and wherein the analysis means comprises an analogue-to-digital converter and a two-state switch means for connecting the input of the analogue-to-digital converter across the two impedances connected in series in a first state of the switch-means and, by way of an amplifier, to a connection between the impedances in a second state of the switch-means, the amplifier having a gain related to the said ratio which allows the analogue-to-digital converter to receive signals over at least most of its input range when the switch means is in its said second state.

9. Apparatus according to claim 8 wherein the impedances are capacitors, one of which is constructed to hold a sample of non-conducting material whose permittivity is to be determined.

10. A method of analyzing the response of a circuit to signals of different frequencies, comprising the steps of generating a series of waveforms in which each waveform has a plurality of frequency components with frequencies in a geometric progression but no other significant frequency components, and the waveforms together having frequency components evenly spaced over a logarithmic spectrum,
applying the series of waveforms to a test circuit, and
repeatedly carrying out a respective Fourier analysis on signals received from the test circuit which result from the application of each of the said waveforms thereto.

* * * * *